(12) United States Patent
Faber et al.

(10) Patent No.: US 10,315,133 B2
(45) Date of Patent: Jun. 11, 2019

(54) METHOD FOR SEPARATING VIRUSES FROM A CONTAMINANT-CONTAINING LIQUID

(75) Inventors: Rene Faber, Goettingen (DE); Martin Leuthold, Goettingen (DE)

(73) Assignee: SARTORIUS STEDIM BIOTECH GMBH, Goettingen (DE)

(*) Notice: Subject to any disclaimer, the term of this patent is extended or adjusted under 35 U.S.C. 154(b) by 346 days.

(21) Appl. No.: 13/821,766

(22) PCT Filed: Aug. 16, 2011

(86) PCT No.: PCT/EP2011/004109
§ 371 (c)(1),
(2), (4) Date: Mar. 8, 2013

(87) PCT Pub. No.: WO2012/041423
PCT Pub. Date: Apr. 5, 2012

(65) Prior Publication Data
US 2013/0164821 A1    Jun. 27, 2013

(30) Foreign Application Priority Data
Sep. 28, 2010 (DE) .................. 10 2010 046 817

(51) Int. Cl.
| | | |
|---|---|---|
| *G01N 30/96* | (2006.01) | |
| *G01N 1/18* | (2006.01) | |
| *B01D 15/36* | (2006.01) | |
| *C12N 7/02* | (2006.01) | |
| *B01D 15/18* | (2006.01) | |
| *C12N 7/00* | (2006.01) | |

(52) U.S. Cl.
CPC ....... *B01D 15/363* (2013.01); *B01D 15/1871* (2013.01); *C12N 7/00* (2013.01); *C12N 7/02* (2013.01); *C12N 2795/14251* (2013.01)

(58) Field of Classification Search
CPC .................................. G01N 30/96; G01N 1/18
USPC .................... 436/177–178, 161; 435/239
See application file for complete search history.

(56) References Cited

U.S. PATENT DOCUMENTS

| | | | | |
|---|---|---|---|---|
| 3,509,070 A | * | 4/1970 | Lapidus ................ | 502/400 |
| 3,655,509 A | * | 4/1972 | Fields .................. | C12N 7/00 210/734 |
| 4,673,733 A | * | 6/1987 | Chandra ............... | A61K 35/16 210/656 |
| 4,935,342 A | * | 6/1990 | Seligson .............. | C07H 1/08 435/270 |
| 5,837,520 A | | 11/1998 | Shabram et al. | |
| 6,005,075 A | * | 12/1999 | Ettlin ................... | B21B 13/06 530/351 |
| 6,008,036 A | | 12/1999 | Fanget et al. | |
| 6,080,571 A | * | 6/2000 | Prior .................... | C07K 14/005 210/660 |
| 6,143,548 A | * | 11/2000 | O'Riordan ............ | C12N 7/00 435/235.1 |
| 6,261,823 B1 | | 7/2001 | Tang et al. | |
| 2002/0037565 A1 | * | 3/2002 | Blanche ................ | C12N 7/00 435/173.9 |
| 2003/0175688 A1 | * | 9/2003 | Pennathur-Das ...... | A61K 48/0091 435/5 |
| 2004/0152183 A1 | * | 8/2004 | O'Riordan ............ | C12N 7/00 435/239 |
| 2004/0251193 A1 | * | 12/2004 | Wu et al. ............. | 210/321.86 |
| 2005/0003507 A1 | * | 1/2005 | Kostel .................. | C12N 7/00 435/239 |
| 2005/0196854 A1 | * | 9/2005 | Konz, Jr. ............. | C12N 7/00 435/239 |
| 2007/0020616 A1 | * | 1/2007 | Lopez .................. | C07K 1/14 435/5 |
| 2007/0207461 A1 | * | 9/2007 | Weggeman ........... | C12N 7/00 435/6.16 |
| 2007/0256970 A1 | * | 11/2007 | DiLeo .................. | B01J 20/327 210/502.1 |
| 2008/0014625 A1 | * | 1/2008 | Etzel ................... | 435/239 |
| 2009/0050566 A1 | * | 2/2009 | Kozlov ................ | B01D 15/1871 210/656 |
| 2010/0059443 A1 | * | 3/2010 | Brellisford .......... | B01D 63/082 210/656 |
| 2010/0093059 A1 | * | 4/2010 | Wolff et al. .......... | 435/239 |

(Continued)

FOREIGN PATENT DOCUMENTS

| | | |
|---|---|---|
| EP | 1 878 791 | 1/2008 |
| WO | 03/078592 | 9/2003 |

OTHER PUBLICATIONS

Mehta et al., "Effect of Membrane Charge on Flow and Protein Transport during Ultrafiltration," Biotechnol. Prog. 22: 484-492 (2006).*
Thomas et al., "A Fast CTAB Method of Human DNA Isolation for Polymerase Chain Reaction Applications," Biochemical Education 25(4): 233-235 (1997).*
Wu et al., "Cationization of Cellulose Fabrics by Polyallylamine Binding," Journal of Applied Polymer Science 100: 1668-1672 (2006)(hereinafter "Wu et al.-2").*
Opitz et al., "Sulfated Membrane Adsorbers for Economic Pseudo-Affinity Capture of Influenza Virus Particles," Biotechnology and Bioengineering, vol. 103, No. 6: 1144-1154 (2009).*
Lapidus, "Purification and Concentration of Influenza Types A and B by Chromatography on Calcium Phosphate," Applied Microbiology, vol. 17, No. 4 (1969).*

(Continued)

*Primary Examiner* — Arlen Soderquist
(74) *Attorney, Agent, or Firm* — Gerald E. Hespos; Michael J. Porco; Matthew T. Hespos

(57) ABSTRACT

The present invention relates to a method for separating viruses from a contaminant-containing liquid medium using two adsorbents having cationic groups, wherein the viruses are adsorbed to the first adsorbent and subsequently eluted and wherein the contaminants present in the resulting eluate are subsequently adsorbed to the second adsorbent. The yield and purity of the viruses obtained as per the method according to the invention is increased by the addition of multivalent anions during the adsorption of the contaminants to the second adsorbent.

15 Claims, No Drawings

(56) References Cited

U.S. PATENT DOCUMENTS

| | | | | |
|---|---|---|---|---|
| 2010/0112001 A1* | 5/2010 | Djurup | ............... | A61K 39/285 424/232.1 |
| 2010/0150961 A1* | 6/2010 | Vedvick | ................ | C12N 7/00 424/216.1 |
| 2011/0142863 A1* | 6/2011 | Iyer | ..................... | C12N 7/00 424/184.1 |
| 2012/0077249 A1* | 3/2012 | Ramaswamy | ............ | C12N 7/00 435/239 |
| 2012/0088228 A1* | 4/2012 | Asher | .................... | C12N 7/00 435/5 |

OTHER PUBLICATIONS

Peterson, E. A. et al, Journal of the American Chemical Society 1956, 78, 751-755.*
Hoyer, B. H. et al, Science 1958, 127, 859-864.*
Levintow, L. et al, Journal of Biological Chemistry 1960, 235, 1960, 70-74.*
Richieri, S. P. et al, Vaccine 1998, 16, 119-129.*
Blanche, F. et al, Gene Therapy 2000, 7, 1055-1062.*
Scherr, M. et al, Gene Therapy 2002, 9, 1708-1714.*
Green, A. P. et al, Human Gene Therapy 2002, 13, 1921-1934.*
Yamada, K. et al, BioTechniques 2003, 34, 1074-1080.*
Smith, R. A. et al, Journal of Virological Methods 2003, 114, 115-124.*
Specht, R. et al, Biotechnology and Bioengineering 2004, 88, 465-473.*
Konz, J. O. et al, Human Gene Therapy 2005, 16, 1346-1353.*
Urabe, M. et al, Molecular Therapy 2006, 13, 823-828.*
Rodrigues, T. et al, Journal of Chromatography B 2006, 837, 59-68.*
Riordan, W. et al, Biotechnology and Bioengineering 2009, 103, 920-929.*
Shabram, P. W. et al, Human Gene Therapy 1997, 8, 453-465.*
Prazeres, D. M. F. et al, Journal of Chromatography A 1998, 806, 31-45.*
Gao, G. et al, Human Gene Therapy 2000, 11, 2079-2091.*
Knudsen, H. L. et al, Journal of Chromatography A 2001, 907, 145-154.*
Teeters, M. A. et al, Journal of Chromatography A 2003, 989, 165-173.*
Branovic, K. et al, Journal of Virological Methods 2003, 110, 163-171.*
Curtis, S. et al, Biotechnology and Bioengineering 2003, 84, 179-186.*
Stadler, J. et al, Journal of Gene Medicine 2004, 6, S54-S66.*
Phillips, M. et al, Journal of Chromatography A 2005, 1078, 74-82.*
Huang, Y. et al, Process Biochemistry 2006, 41, 2320-2326.*
Kalbfuss, B. et al, Biotechnology and Bioengineering 2007, 96, 932-944.*
Qu, G. et al, Journal of Virological Methods 2007, 140, 183-192.*
Kramberger, P. et al, Journal of Chromatography A 2007, 1144, 145-149.*
Wu, C. et al, Human Gene Therapy 2007, 18, 665-672.*
Smrekar, F. et al, Journal of Chromatography B 2008, 861, 177-180.*
Vicente, T. et al, Journal of Membrane Science 2008, 311, 270-283.*
Strauss, D. M. et al, Biotechnology and Bioengineering 2009, 102, 168-175.*
Gutierrez-Aguirre, I. et al, Journal of Chromatography A 2009, 1216, 2700-2704.*
Whitfield, R. J. et al, Journal of Chromatography A 2009, 1216, 2725-2729.*
Wolff, M. W. et al, Biotechnology and Bioengineering 2010, 105, 761-769.*
Kramberger, P. et al, Journal of Virological Methods 2010, 166, 60-64.*
B. Kalbfuss—"Downstream Processing of Influenza Whole-Virions for Vaccine Production"—University of Magdeburg dissertation 2009.
B Kalbfuss et al.—"Direct capture of influenza A virus from cell culture supernatant with Sartobind anion-exchange membrane adsorbers"—Journal of Membrance Sciense 299 (2007)—pp. 251-260.
T. Vicente et al.—"Purification of recombinant baculoviruses for gene therapy using membrane processes"—Gene Therapy 2009—pp. 1-10.
I. Tatarova et al.—"Characterization of pore structure of a strong anion-exchange membrane adsorbent under different buffer and sals concentration conditions"—Journal of Chromatography A 1216 (2009)—pp. 941-947.
International Search Report dated Nov. 4, 2011.
International Preliminary Report on Patentability, dated Apr. 2, 2013.

* cited by examiner

METHOD FOR SEPARATING VIRUSES FROM A CONTAMINANT-CONTAINING LIQUID

BACKGROUND

1. Field of the Invention

The present invention relates to a method for separating viruses from a contaminant-containing liquid medium, wherein the viruses are first adsorbed to a first adsorbent having cationic groups and subsequently desorbed therefrom and wherein subsequently a liquid medium containing the viruses and contaminants is contacted with a second adsorbent having cationic groups in order to adsorb the contaminants.

2. Description of the Related Art

Efficient methods for separating viruses from biotechnological liquids, which frequently contain undesired contaminants, are becoming increasingly important in medicine and biotechnology.

Viruses, virions or viral particles consist of a nucleic acid (deoxyribonucleic acid (DNA) or ribonucleic acid (RNA)) and a protein coat, also termed a capsid. Some viruses are additionally surrounded by a membrane, which is referred to as a viral envelope, or have other additional constituents. Such viruses which have a viral envelope in addition to the capsid are termed enveloped, and viruses without such an envelope are referred to as nonenveloped. Viroids have neither a capsid nor a viral envelope. A virus itself is not capable of metabolic processes, and it therefore requires host cells for propagation. Viruses attack the cells of eukaryotes (plants, fungi, animals) and prokaryotes (bacteria and archaea). Viruses which utilize prokaryotes as hosts are termed bacteriophages.

The influenza virus is an enveloped virus particle having a diameter of from 80 to 120 nm, in the envelope of which differing numbers of proteins and glycoproteins are embedded. The genome of almost all influenza viruses consists of eight negative-sense RNA segments. The main proteins of the envelope are hemagglutinin (HA) and neuraminidase (NA). Viral mutations, particularly with respect to possible alterations to hemagglutinin, can considerably increase the risk of infection for the potential host.

Virus-like particles (VLPs) are virus particles which are produced by biotechnological means. They do not contain any viral nucleic acids and are therefore not capable of multiplying in the target cells. VLPs are required in virology and in immunology for studying viruses and cellular functions. These particles are not empty, since they would otherwise become unstable; instead they are packed with either, nonspecifically, nucleic acids or with nonfunctional DNA or RNA. In addition, proteins can be packed in a specific manner.

Natural and/or recombinant viruses can be used as vaccines in medicine. Vaccines are preventative or therapeutic agents which bring about their effect by stimulating the immune system of an individual. Live attenuated vaccines contain weakened viruses which can still multiply and induce an immune response, i.e., are immunogenic, but do not generally cause a disease, i.e., are not pathogenic. Dead vaccines contain inactivated or killed viruses or constituents of viruses.

Another way of using viruses in medicine is to be found in gene therapy. Gene therapy refers to the insertion of genes into the cells of an individual for the treatment of inherited diseases or gene defects. The introduction of said genes can compensate for a gene defect. A gene defect is present when a living being lacks a gene or has a mutation which results in the gene product (e.g., a protein) not being formed or not being able to carry out its function properly. During gene therapy, cells are removed from the body. Said cells receive the new (therapeutic) gene and are subsequently reintroduced into the body (ex vivo). The use of viral vectors makes it possible to carry out gene therapy directly in the body (in vivo). Here, retroviruses or adenoviruses are used in most cases for transferring DNA segments into the somatic cells of the patient.

The production of viruses which are used either as vaccines or as vectors in gene therapy is of increasing relevance to biotechnology. Production is carried out in several steps:
1. generating a pathogen/antigen,
2. producing the antigen in an appropriate system (e.g., cell culture, chick embryos),
3. purifying the antigen and
4. formulating the vaccine or the vector by addition of auxiliary agents, adjuvants, stabilizers, preservatives, etc.

After culturing viruses in cell cultures (e.g., MRC-5, vero, PER.C6) or in chicken eggs, it is necessary to separate the viruses from the contaminants (e.g., host cell proteins, DNA or endotoxins) in order to obtain them in a pure form for the desired application. Moreover, it is advantageous to separate infectious molecules or particles from noninfectious ones. Viral properties, such as the isoelectric point (pI), surface hydrophobicity, presence of an envelope and the hydrodynamic diameter, can be used for the purposes of the purification. Purification methods based on the size of the viruses are known in the prior art. They include, for example,

- density-gradient ultracentrifugation (in a CsCl or sucrose gradient; the high capital costs are a disadvantage),
- ultrafiltration and microfiltration using planar or hollow-fiber membranes,
- precipitation (e.g., using polyethylene glycol or ammonium sulfate) or
- size-exclusion chromatography using chromatography gels, for example based on agarose. The disadvantages of the last-mentioned method are low flow rates and the low process speed.

For the degradation of host-cell DNA, an enzyme, for example the endonuclease BENZONASE®, is often used. The disadvantage of this method is the very high enzyme costs. Depth filters are used to remove cells and/or cell fragments when purifying viruses.

The adsorption of viruses to solid phases as a result of chromatographic purification is of great significance in virus purification, especially on a process scale. Adsorbents are porous solids which can bind selectively to particular components of fluids via functional surface groups referred to as ligands. Target substance(s) and/or contaminant(s) are referred to as adsorbands, and they can also be several different substances. Adsorbands can be individual molecules, associate or particles and are preferably viruses, viral constituents, virus-like particles, proteins or other substances of biological origin.

The binding of the adsorbands to the adsorbent can be reversible or irreversible, and in any case it allows the separation thereof from the fluids, which are generally aqueous liquids and are termed media hereinafter. The term "elution" covers the desorption of an adsorband from the adsorbent and the associated wash steps, etc. The liquid used for the elution is the eluent. The components can be one or more target substances and/or one or more contaminants. Target substances are valuable substances which are to be obtained in enriched or pure form from the medium. Target substances can, for example, be viruses. Contaminants are substances whose absence or removal from the fluid is necessary or desirable for technical, regulatory or other reasons. Contaminants can, for example, be host-cell proteins, amino acids, nucleic acids, endotoxins, protein aggregates, ligands or parts thereof. For the removal of contaminants, which is referred to as "negative adsorption" (also termed "flow-through" (FT)), the adsorption can/must proceed irreversibly if the adsorbent is to be used only once. In the case of the adsorption of target substance(s), the process has to proceed reversibly (also termed "bind-and-elute" (B&E)). Either a mere enrichment or a separation into several target substances can be carried out, and in the latter case either the adsorption, the desorption or both can be done selectively.

Conventional adsorbents for chromatography are particulate in form and are operated in the form of packings in columns. Since viruses are typically up to 1000 nm in size, conventional chromatography gels having pore sizes in the range of 30-400 nm are usually unsuitable for virus purification. The viruses can only bind to the outer surface of the particles, and as a result only low binding capacities are achieved. Various ligands have already been used in virus purification: anion exchangers (AEX), cation exchangers (CEX), affinity ligands (AF), ligands for hydrophobic interaction chromatography (HIC) or complexing ligands for immobilized metal ion affinity chromatography (IMAC).

In the prior art, numerous methods for separating viruses from biotechnological fluids by means of various chromatography matrices having ion-exchanging ligands have been described.

WO 03/078592 A2 describes a method for purifying adenoviruses, obtained from cell lysates, by means of two anion-exchanger filters. The adenovirus is first bound reversibly in "bind-and-elute" mode on a first anion-exchange filter. Thereafter, the eluate obtained is bound reversibly in "bind-and-elute" mode on a second anion-exchange filter following nuclease treatment to degrade nucleic acid contaminants.

U.S. Pat. No. 6,261,823 B1 describes a method for purifying adenoviruses by means of a first anion-exchanger chromatography step using DEAE Fractogel followed by a second size-exclusion chromatography step using the gel Superdex 200. The virus is adsorbed reversibly in "bind-and-elute" mode on the anion exchanger and subsequently eluted in the first step.

U.S. Pat. No. 5,837,520 describes a method for purifying viral vectors obtained from cell lysates following treatment with nucleic acid-cleaving enzymes. In a first step, the viral particles are treated by means of a first cation- or anion-exchanging chromatography gel and, in a second step, they are treated with an affinity chromatography gel on which metal ions capable of chelating are immobilized. Alternatively, in the second step, a chromatography step based on hydrophobic interactions can be carried out.

U.S. Pat. No. 6,008,036 describes a method for virus purification by means of two ion exchangers in two steps, with an anion-exchanging chromatography matrix being used for the second step when a cation-exchanging matrix is used in the first step, and vice versa.

EP 1 878 791 A1 describes the purification of influenza viruses by means of various anion exchangers, including gels, monoliths and membrane adsorbers. The described method provides only low yields in the region of not more than 50% for influenza viruses.

B. Kalbfuss et al. disclose in "Journal of Membrane Science", 299 (2007), 251-260, the purification of influenza A viruses from cell cultures by means of Sartobind® D MA75 and Sartobind® Q anion-exchange membranes. The virus is bound reversibly to this strong or weak anion exchanger and subsequently eluted. To increase the selectivity of the respective membrane for viruses, the authors propose placing upstream of the anion-exchange step a pretreatment step in which the accompanying contaminants consisting of nucleic acids are separated from the influenza viruses.

B. Kalbfuss (University of Magdeburg dissertation (2009): "Downstream Processing of Influenza Whole-Virions for Vaccine Production") reports on the binding of influenza viruses to a Sartobind® Q membrane adsorber, which is a strong anion exchanger, in comparison with the binding of said viruses to a Sartobind® D membrane adsorber, which is a weak anion exchanger. The virus yields when using the Sartobind® Q membrane adsorber are, at 86%, greater than the virus yields which are achieved when using the Sartobind® D membrane adsorber (38%). The low isoelectric point of the accompanying contaminants (DNA) allows the strong adsorption thereof. By adjusting the pH and ionic strength, DNA can be adsorbed, with the viruses being conducted through the anion exchanger without being adsorbed. In experiments to separate DNA as contaminants from influenza viruses, it was found that very high salt concentrations are required in order to suppress the virus adsorption. At a concentration of 0.15 M NaCl, the virus adsorbs completely to the membrane adsorber, and, at a concentration of 0.7 M NaCl, 10% of the virus was adsorbed to Sepharose® Q XL. However, the high salt concentration leads to the breakthrough of DNA.

The convectively permeable chromatographic materials known in the prior art, such as membrane adsorbers (e.g., Sartobind® product line from Sartorius Stedim Biotech GmbH) or monoliths from BIA Separations, were originally developed and optimized for protein purification, the aim being high binding capacities for proteins. When purifying viruses, the intention is to remove proteins (e.g., host-cell proteins or endotoxins) or nucleic acids, as contaminants, from the virus, as target product. When using the aforementioned methods known in the prior art using ion exchangers, not only the viruses but also the aforementioned contaminants are adsorbed, and this leads to low purities and low virus yields following the desorption of the virus from the membrane adsorber.

T. Vicente et al. describe in "Gene Therapy" 2009, 1-10, a three-stage method for purifying baculoviruses, comprising an opening step of depth filtration, a second step of ultrafiltration or diafiltration and a final step of purification of baculoviruses by means of reversible binding to a Sartobind® D MA15 anion-exchanger membrane adsorber.

It is an object of the present invention to provide a method which overcomes the aforementioned disadvantages of the prior art (low purity of the viruses owing to the presence of contaminants and low yields of viruses) and which makes it possible to provide viruses from biotechnological fluids in high yields and high purity in a rapid and cost-saving manner.

SUMMARY OF THE INVENTION

The present invention provides a method for separating viruses from a contaminant-containing liquid medium, comprising the following steps:
A) contacting the liquid medium with a first adsorbent containing cationic groups,
B) separating the liquid medium from the first adsorbent,
C) desorbing the viruses from the first adsorbent, D) contacting a second adsorbent containing cationic groups with a liquid medium comprising the viruses from step C) and multivalent anions, and E) separating the virus-containing liquid medium from step D) from the second adsorbent.

According to the present invention, the term "virus" is not subject to any specific restriction and concerns all viruses which are accessible by biotechnological methods, for example by cell lysis of cell cultures. It includes, for example, wild-type, mutant and recombinant viruses, adenoviral and retroviral vectors for the expression of heterologous nucleic acid sequences, baculoviruses, bacteriophages, viral constituents and virus-like particles.

According to the present invention, the term "contaminants" concerns all contaminants which may be present as (undesired) accompanying components in media, for example following cell lysis of a cell culture, in addition to the viruses to be removed, for example host-cell proteins, endotoxins, nucleic acids (DNA, RNA) and cellular constituents.

According to the invention, in step D), the second adsorbent is contacted with a liquid medium comprising the viruses from step C) and multivalent anions in order to separate the contaminants from the viruses by adsorption to the second adsorbent.

It was found that, surprisingly, the efficiency of the anion exchangers used in step A) and D) with regard to the removal of contaminants, such as DNA, host-cell proteins or endotoxins, from virus-containing solutions can be significantly increased when multivalent ions are added to the medium which is used in step D), i.e., the virus-containing buffer, and which results following step C). The increase in efficiency owing to the addition of the multivalent ions in step D) is manifested in shortened process times, higher virus yields and higher virus purity. Owing to the combination according to the invention of two anion exchangers, of which the first is operated in "bind-and-elute" mode and the second is operated in "flow-through" mode, it is possible to provide a purification process for viruses which has the aforementioned advantages over the methods known from the prior art.

In the context of the present invention, "multivalent anions" are to be understood to mean all anions having at least two ionogenic charges. As a source for such anions, all appropriate inorganic or organic salts which are soluble in water or aqueous solutions can be used.

According to the present invention, the "first adsorbent" and the "second adsorbent" are selected from the group of the chromatography matrices comprising adsorption membranes, gels and monoliths.

In a preferred embodiment, different chromatography matrices are used for the first and the second adsorbent.

In an alternative embodiment, identical chromatography matrices are used for the first and the second adsorbent.

With respect to the aforementioned chromatography matrices, adsorption membranes in particular are preferred. According to the invention, adsorption membranes are understood to mean planar adsorbents having pores passing from one side to the other side, whose surface is functionalized by all known positively charged natural or synthetic ligands. The adsorption membranes used for the method according to the invention can be present in modules whose designs correspond to the forms common in membrane filtration (e.g., spiral-wound module, stacked module, etc.). Particular preference is given to convectively permeable adsorption membranes which, in contrast to particulate adsorbents, have the advantage that application of a hydraulic pressure difference between the two sides of its surface can force flow-through with a medium, and as a result, instead of purely diffuse transport of the adsorbands in the direction of a concentration gradient into the interior of the adsorption membrane, convective transport is achieved which, at a high flow rate, can be effected very much more rapidly than diffusive mass transfer per se. As a result, it is possible to avoid one disadvantage inherent to the particulate adsorbents, which is referred to as "diffusion limitation", which is that with increasing particle size of the adsorbent and increasing molar mass of the adsorband the time required to set the adsorption equilibrium increases considerably, worsening the kinetics. In addition, the advantage is that the pores are accessible to large molecules and particles, for example viruses. Thus—unlike in the case of particulate chromatography gels—viruses can reach the ligands on the entire inner and outer surface of the adsorption membrane.

Preference is given to embodiments in which the adsorption membrane is a microporous membrane consisting of a cellulose derivative, polyamide, poly(ether)sulfone, polyvinylidene difluoride, polyacrylonitrile, polyvinyl chloride, polypropene, polyethene, polytetrafluoroethene, copolymers thereof or mixtures thereof.

According to the invention, the first and the second adsorbent have cationic groups selected from the group of the primary, secondary, tertiary and quaternary ammonium groups and combinations thereof. Particular preference is given to tertiary ammonium groups selected from the group of the trialkylammonium and triarylammonium groups and to primary ammonium groups selected from the group of the polymeric amino compounds having linear and/or branched and/or cyclic structures. In the case of the polymeric amino compounds, ligands selected from the group of polyallylamine, polyethyleneimine and polyvinylamine are preferred the most. An example of an adsorbent functionalized with a polyallylamine ligand is the adsorption membrane of example 21 that is referred to in WO 2009/127285 A1.

The first and the second adsorbent can both contain the same cationic groups or can contain different cationic groups in each case.

DETAILED DESCRIPTION OF THE PREFERRED EMBODIMENTS

According to a preferred embodiment of the present invention, particular preference is given to the multivalent anions selected from the group comprising orthophosphate, monohydrogendiphosphate, citrate, carbonate, nitride, oxide, sulfide, sulfite and sulfate and combinations thereof.

More particularly, it was found that the addition of trivalent anions, such as orthophosphate or citrate, greatly reduces phage binding to the second adsorbent, while the binding of undesired contaminants (for example DNA or endotoxins) to the second adsorbent is hardly affected. This surprising finding is utilized in the method according to the invention to remove the aforementioned contaminants from virus-containing solutions according to "negative adsorption" ("flow-through" step) by means of the second adsorbent in step D). The addition of said trivalent anions can increase the selectivity of the adsorbents used in the method according to the invention in support of higher virus purities.

With respect to the aforementioned multivalent anions, the orthophosphate anion having three negative charges is preferred the most. When using said anion, particularly high virus yields and virus purities are achievable (cf. example).

In a further preferred embodiment of the present invention, the charge density of the cationic groups on the first and/or the second adsorbent is less than 120 μmol/ml, preferably less than 100 μmol/ml, particularly preferably less than 80 μmol/ml and most preferably less than 50 μmol/ml.

In a particularly preferred embodiment, the charge density of the cationic groups on the first adsorbent is less than 120 μmol/ml, preferably less than 100 μmol/ml, particularly preferably less than 80 μmol/ml and most preferably less than 50 μmol/ml.

The last-mentioned embodiment of the method according to the invention, wherein the first adsorbent used according to the invention in "bind-and-elute" mode in steps A) to C) has the aforementioned limiting of the charge density of the cationic groups, makes it possible, in synergy with the use of multivalent anions for carrying out step D) in "flow-through" mode, to separate viruses in a particularly high yield and purity from accompanying contaminants from the cell lysis of a cell culture.

R. Faber et al. have shown in "Journal of Chromatography A" 1216 (2009), 941-947, that molecules which are approximately 100 nm in size cannot enter the grafted-on gel layer of adsorption membranes. As a result, particles of such a size can only be adsorbed on the outer surface of the gel layer. However, the grafted gel layer is accessible to protein molecules which are smaller in size than viruses, i.e., are about 10 nm in size, and as a result the proteins can be adsorbed in large amounts in the three-dimensional gel layer.

The aforementioned embodiment of the method according to the invention having limited charge density on the first adsorbent shows that, surprisingly, as a further development of the findings of R. Faber et al., charge densities below 120 μmol/ml do not affect the binding of large molecules, such as viruses to be removed, to the first adsorbent in "bind-and-elute" mode, whereas the binding of the contaminants (host-cell proteins, DNA fragments) to the first adsorbent is favorably further reduced and the purity of the viruses obtained as per the method according to the invention can thus be increased.

In a further embodiment of the method according to the invention, intermediate treatment steps are carried out after step C) and before step D). The intermediate treatment steps are preferably tangential flow filtration, ultrafiltration or diafiltration steps, dilution steps, centrifugation steps, precipitation reactions, chromatography steps, enzyme treatment steps (e.g., with nucleases) or combinations thereof.

In an alternative embodiment of the method according to the invention, the sequence of the steps according to claim 1 can be altered such that steps D) and E) precede steps A) to C). In this case, the contaminants are first removed from the virus-containing medium in the presence of multivalent anions by the first adsorbent by means of "negative adsorption" in "flow-through" mode, and the resulting permeate is subsequently contacted with the second adsorbent to adsorb the viruses and the viruses are subsequently desorbed from the second adsorbent.

The present invention and further resulting advantages will now be more particularly elucidated with reference to the embodiments described in the example, without restricting the scope of the claims for which protection is sought to said embodiments.

EXAMPLE

Purification of ΦX174 Bacteriophages as Model Viruses

The model virus used is the bacteriophage ΦX174, which has a diameter of about 30 nm and an isoelectric point pI of 6.4-6.7. For the removal of the contaminants (DNA), anion exchangers from Sartorius Stedim Biotech GmbH (membrane A: Sartobind® Q; membrane B: polyallylamine-modified cellulose membrane as described in example 21 of WO 2009/127285 A1) are used as first and second adsorbent containing cationic groups. Two different combinations of anion exchangers were used:

combination 1): first adsorbent: membrane A; second adsorbent: membrane A; and combination 2): first adsorbent: membrane A; second adsorbent: membrane B.

During steps A) and B) of the method according to the invention, the phages are adsorbed on membrane A and subsequently desorbed in step C). This corresponds to a "bind-and-elute" step. Subsequent steps D) and E) are carried out with either membrane A or B as "negative adsorption" in "flow-through" mode.

Culturing the Phages

The phages are produced in a culture of *Escherichia coli* C (ATCC 13706). After the bacterial culture has been cultivated in a disposable bioreactor (50 l BIOSTAT® CULTIBAG®, Sartorius Stedim Biotech GmbH, Göttingen, Germany) and inoculated, culturing is carried out for 4 h. Subsequently, culturing is ended. Via a filtration cascade (Sartopure® PP2 MidiCap 8 μm-5 μm and Sartopore® 2XLG 0.8-0.2 μm, Sartorius Stedim Biotech GmbH), the phages are filtered such that they become particle-free and sterile. The final volume is reduced to 600 ml by crossflow filtration (SARTOCON® Slice Cassette 30 kDa, Sartorius Stedim Biotech GmbH). This solution is mixed with a 30% aqueous polyethylene glycol solution and subsequently centrifuged for 90 min at 8430 rpm (SORVALL RC-6 centrifuge, Thermo Fisher Scientific, Bonn, Germany). The pellets are resuspended using 25 ml of 25 mM Tris buffer solution (tris(hydroxymethyl)aminomethane, pH=8.0), aliquoted, and stored at −70° C. This stock solution is the starting material for the example elucidated here and is diluted accordingly as required.

The phage titer is determined by titration. To this end, the samples are appropriately diluted and mixed with the host organism (*Escherichia coli* C). After an incubation time of 10 min, the samples are plated out and incubated overnight at 37° C. On the following day, the plaques are counted and the titer is calculated. Determination of DNA concentration for the second process step in the example is carried out according to manufacturer's instructions with "PicoGreen" (QUANT-IT® PicoGreen dsDNA reagent P7581, Life Technologies, Carlsbad, USA) using a plate reader (TECAN SAFIRE, Tecan Trading AG, Switzerland). Fluorescence was measured with excitation at 480 nm and absorption at 520 nm (GREINER FLUOTRAC® 200, Greiner Bio-One GmbH, Frickenhausen, Germany). For each experiment, membranes A or B are integrated as a triple layer into a holder. The total area of the membranes was 15 cm$^2$.

Adsorption and Desorption of the Phages/Steps A) to C) of the Method According to the Invention In the first step, the stock solution is diluted 1:100 with 20 mM Tris buffer (pH=8.1). The phage-containing, liquid medium having a phage titer of 6×10$^7$ PFU/ml is contacted with membrane A, with the phages adsorbing to the membrane (PFU="plaque-forming units"). In all steps, filtration is performed at a flow rate of 20 ml/min using a peristaltic pump. Prior to filtration, membrane A is conditioned with 10 ml of buffer (1 M sodium chloride, 20 mM Tris [tris(hydroxymethyl)aminomethane], pH=8.1) and washed with 10 ml of binding buffer (20 mM Tris, pH 8.1). Subsequently, 800 ml of the phage solution in binding buffer are filtered (loading, contacting the liquid medium with adsorbent). After loading, membrane A is washed again with 30 ml of binding buffer. In addition, an elution medium (250 ml of 150 mM sodium chloride in binding buffer) is applied to membrane A. Table 1 shows the phage concentrations in PFU/ml (plaque-forming units per ml of solution) in individual fractions. Owing to the analytical variations in the measurement method, the recovery rate is, following the elution of the phages from the first adsorbent (=membrane A), more than 100%, in this case 119%, i.e., as per step C) of the method according to the invention, the phages can be quantitatively eluted from the first adsorbent, i.e., the yield thereof is practically 100%.

TABLE 1

Phage concentration and recovery rate as per step C)

| | Phage concentration PFU/ml | Recovery % |
|---|---|---|
| Loading | $6.18 * 10^7$ | 100 |
| Flow-through | $7.76 * 10^3$ | 0.013 |
| Washing | $9.33 * 10^2$ | 0.001 |
| Elution | $2.34 * 10^8$ | 119 |

"Negative Adsorption" of the Contaminants in "Flow-Through" Mode to the Second Adsorbent (Steps D) and E)) of the Method According to the Invention DNA can be detected by means of the "PicoGreen" method even in the phage-containing eluate obtained as per step C) of the method according to the invention (about 200 ng/ml). This may be free fragments of the phage DNA or host-cell DNA from culturing of *Escherichia coli*. By diluting the concentrated elution solution (dilution of the phage concentration of $2.34*10^8$ PFU/ml, cf. table 1, to $1.00*10^7$ PFU/ml) after carrying out step C) of the method according to the invention, the DNA concentration is reduced, and as a result the DNA detection limit of the "PicoGreen" method is approached.

In order to demonstrate that the method according to the invention in the "flow-through" mode of steps D) and E) allows the efficient separation of viruses from contaminants even from stock solutions containing a high load of contaminants from the preceding cell lysis, salmon sperm DNA, lot 8087, from Biomol GmbH, Hamburg is added as model contaminant to the eluate obtained as per step C). Here, a concentration of 200 ng/ml of this model DNA is set. The concentration of DNA in the phage-containing solution used for steps D) and E) thus corresponds to the concentration of DNA in the elution solution obtained as per step C).

The following results provide evidence that the method according to the invention allows separation of phages from contaminants from a biotechnological stock solution in a high yield and purity, even if the eluate, despite steps A) to C) in which some of the contaminants are already removed by the first adsorbent, is added with a high contaminant load to the second adsorbent.

Subsequent steps D) and E) are carried out according to the invention as "negative adsorption" in "flow-through" mode. The two main components in the eluate from step C) (phage as target substrate, and salmon sperm DNA as contaminants) have a negative net charge in the neutral pH range and bind to the positively charged membranes A (combination 1)) or B (combination 2), cf. page 21), with the separation of the phages from the contaminants being made possible by the addition of sodium orthophosphate as a multivalent anion source.

For steps D) and E), two variants (combination 1) and combination 2), cf. S. 21) are described below:

Membrane A (Combination 1))

For membrane A, part of the elution solution as per step C) was appropriately diluted in order to obtain an NaCl concentration of 6 mM in 20 mM Tris buffer at pH 7.5. The phage titer is thereafter $1\times10^7$ PFU/mL.

Membrane B (Combination 2))

For membrane B, the remaining part of the elution solution as per step C) was likewise set to a phage titer of $1\times10^7$ PFU/mL, with the NaCl concentration of 150 mM (in 20 mM Tris buffer at pH 7.5) remaining constant. The phage titer is thereafter $1\times10^7$ PFU/mL.

Each of 4 different buffer compositions are tested. The behavior of the second adsorbent upon addition of 0, 2, 10 and 30 mM sodium orthophosphate to the phage-containing medium comprising the eluate from step C) (cf. table 2) is characterized.

TABLE 2

| Buffer composition | Membrane A | Membrane B |
|---|---|---|
| Monovalent anion, chloride [mM] | 6 | 150 |
| Multivalent anion, orthophosphate [mM] | 0-30 | 0-30 |
| TRIS [mM] | 20 | 20 |

After the wash step with 50 mL of binding buffer, 150 ml of the mixture of phage solution and DNA solution were filtered at a flow rate of 10 ml/min. By analyzing the concentrations of the individual components in the starting solutions and flow-through fractions, it is possible to characterize the retention for both the DNA and the phages (cf. table 3).

TABLE 3

Percentage (%) of the starting concentration of phages and contaminants (DNA) in the flow-through as per step E) of the method according to the invention

| Orthophosphate concentration [mM] | Comb. 1) Membrane A Phage | Comb. 1) Membrane A DNA | Comb. 2) Membrane B Phage | Comb. 2) Membrane B DNA |
|---|---|---|---|---|
| 0 | 0.001 | <1 | <0.00001 | <1 |
| 2 | 0.001 | <1 | 0.0001 | <1 |
| 10 | 0.01 | <1 | 0.001 | <1 |
| 30 | 59-78 | <1 | 75-83 | <1 |

For all tested buffer configurations, the measured concentration of DNA in the samples of the permeate stream as per step E) is less than 1% of the DNA concentration of the starting solution. For the contemplated buffer compositions, the binding of DNA to the ion-exchanger membranes A and B remains approximately constantly high. The nonbinding conditions for the phages, under which the phages can be obtained in a high yield, are achieved at a sodium orthophosphate concentration starting from 30 mM.

The invention claimed is:

1. A method for separating viruses from a virus and contaminant-containing liquid medium, comprising:
    diluting the virus and contaminant-containing liquid medium with a binding buffer solution;

contacting the virus and contaminant-containing liquid medium with a first adsorption membrane that includes cationic groups, then separating the contaminant-containing liquid medium from the first adsorption membrane, then quantitatively eluting the viruses from the first adsorbent with a monovalent salt and binding buffer solution, and thereby forming a second liquid medium that includes the viruses, and then adding multivalent anions consisting of divalent and/or trivalent anions to the second liquid medium that includes the viruses, then flowing the second liquid medium that includes the viruses and that has the multivalent anions therein through a second adsorption membrane that includes cationic groups, and then collecting the second liquid medium with the viruses, wherein:

the charge density of the cationic groups on the first adsorption membrane is less than 50 μmol/ml; and the first adsorption membrane has, as cationic groups, trimethylammonium groups and the second adsorption membrane has, as cationic groups, trimethylammonium groups or ammonium groups based on polyallylamine ligands.

2. The method as claimed in claim 1, wherein different chromatography matrices are used for the first and the second adsorption membrane.

3. The method as claimed in claim 1, wherein identical chromatography matrices are used for the first and the second adsorption membrane.

4. The method as claimed in claim 1, wherein the adsorption membranes are microporous membranes selected from the group consisting of a cellulose derivative, polyamide, poly(ether)sulfone, polyvinylidene difluoride, polyacrylonitrile, polyvinyl chloride, polypropene, polyethene, polytetrafluoroethene, copolymers thereof or mixtures thereof.

5. The method as claimed in claim 1, wherein the charge density of the cationic groups on the second adsorption membrane is less than 50 μmol/ml.

6. The method as claimed in claim 1, further comprising at least one intermediate treatment step.

7. The method as claimed in claim 6, wherein the intermediate treatment step is selected from the group consisting of a tangential flow filtration, an ultrafiltration or diafiltration, a dilution, a centrifugation, a precipitation reaction, a chromatography step, an enzyme treatment and combinations thereof.

8. The method as claimed in claim 1, wherein the cationic groups of the first and the second adsorption membrane are selected from the group comprising primary, secondary, tertiary and quaternary ammonium groups and combinations thereof.

9. The method as claimed in claim 1, wherein the contaminants are selected from the group comprising cell-culture constituents, nucleic acids, endotoxins and host-cell proteins.

10. The method of claim 1, wherein the multivalent anions are added to the second liquid medium to a concentration of at least 30 mM.

11. The method of claim 1, wherein the binding buffer is Tris.

12. The method as claimed in claim 1, wherein the multivalent anions consist of phosphate ($PO_4^{3-}$) and/or citrate ($C_6H_5O_7^{3-}$) trivalent anions.

13. The method as claimed in claim 1, wherein the multivalent anions consist of sulfate ($SO_4^{2-}$), sulfite ($SO_3^{2-}$), and/or carbonate ($CO_3^{2-}$) bivalent anions.

14. The method as claimed in claim 1, wherein the multivalent anions consist of phosphate ($PO_4^{3-}$), citrate ($C_6H_5O_7^{3-}$), sulfate ($SO_4^{2-}$), sulfite ($SO_3^{2-}$), and/or carbonate ($CO_3^{2-}$) anions.

15. A method comprising:

providing a liquid medium that includes viruses and contaminants in a binding buffer;

forming a virus-adsorbed membrane by contacting the liquid medium with a virus-adsorbent microporous membrane that includes cationic groups;

separating the liquid medium from the virus-adsorbed membrane;

washing the virus-adsorbed membrane with the binding buffer;

quantitatively eluting the viruses from the adsorbent membrane with a monovalent anion solution to provide a virus-containing eluent; and then adding a phosphate ($PO_4^{3-}$) and/or citrate ($C_6H_5O_7^{3-}$) trivalent anion to the virus-containing eluent to provide a trivalent anion solution with a trivalent anion concentration of at least 30 mM;

filtering the trivalent anion solution through a non-binding microporous membrane that includes ammonium groups based on polymers selected from polyallylamine, polytheylene imine, and polyvinylamine; wherein:

the eluted trivalent anion solution from the filtering of the trivalent anion solution, includes the viruses and less than 1% of nonenveloped nucleic acids:

the charge density of the cationic groups on the virus-adsorbent microporous membrane is less than 50 μmol/ml; and the virus-adsorbent microporous membrane has, as cationic groups, trimethylammonium groups and the second adsorption membrane has, as cationic groups, trimethylammonium groups or ammonium groups based on polyallylamine ligands.

* * * * *